United States Patent [19]

Bales et al.

[11] Patent Number: 4,723,550
[45] Date of Patent: Feb. 9, 1988

[54] LEAKPROOF HEMOSTASIS VALVE WITH SINGLE VALVE MEMBER

[75] Inventors: Thomas O. Bales, Coral Gables; J. William Box, Miami; Keith Reisinger, Miami Lakes, all of Fla.

[73] Assignee: Cordis Corporation, Miami, Fla.

[21] Appl. No.: 928,828

[22] Filed: Nov. 10, 1986

[51] Int. Cl.$^4$ ............................................. A61M 29/02
[52] U.S. Cl. .................................. 128/344; 128/348.1; 604/256
[58] Field of Search ................. 604/256, 167, 9, 169; 277/207 R, 116.2, 117, 118; 128/344, 348.1

[56] References Cited

U.S. PATENT DOCUMENTS

| | | |
|---|---|---|
| 3,180,334 | 4/1965 | Glenn . |
| 4,000,739 | 1/1977 | Stevens . |
| 4,177,814 | 12/1979 | Knepshield et al. . |
| 4,240,411 | 12/1980 | Hosono . |
| 4,303,222 | 12/1981 | Campbell . |
| 4,424,833 | 1/1984 | Spector et al. . |
| 4,430,081 | 2/1984 | Timmermans . |
| 4,475,548 | 10/1984 | Muto ............................... 604/167 X |
| 4,493,710 | 1/1985 | King et al. . |

FOREIGN PATENT DOCUMENTS 3042229 5/1982 Fed. Rep. of Germany ...... 604/167

Primary Examiner—Michael H. Thaler
Attorney, Agent, or Firm—George H. Gerstman

[57] ABSTRACT

A hemostasis valve in which the valve member is a tubular, resilient gasket which may be compressed with variable pressure to provide a variable pressure seal to an elongated member extending through the tubular bore of the gasket. The gasket bore also defines at least one resilient, annular rib whereby the elongated member passing through the tubular gasket bore may be subjected at all times to at least a relatively low pressure seal from the resilient, annular rib, irrespective of the pressure of the variable pressure seal. Additionally, the pressure on the gasket may be applied and released by means of a pressure member positioned against the gasket. Structure is provided permitting longitudinal motion, but preventing rotational motion, of the pressure member. A rotatable cap is provided, with facing, mating spiral track means carried on both the inner face of th rotatable cap and outer face of the pressure member, to cause pressurizing advancement of the pressure member against the tubular gasket by rotation of the cap in one direction, and release of such pressurizing advancement by rotation of the cap in the other direction.

7 Claims, 5 Drawing Figures

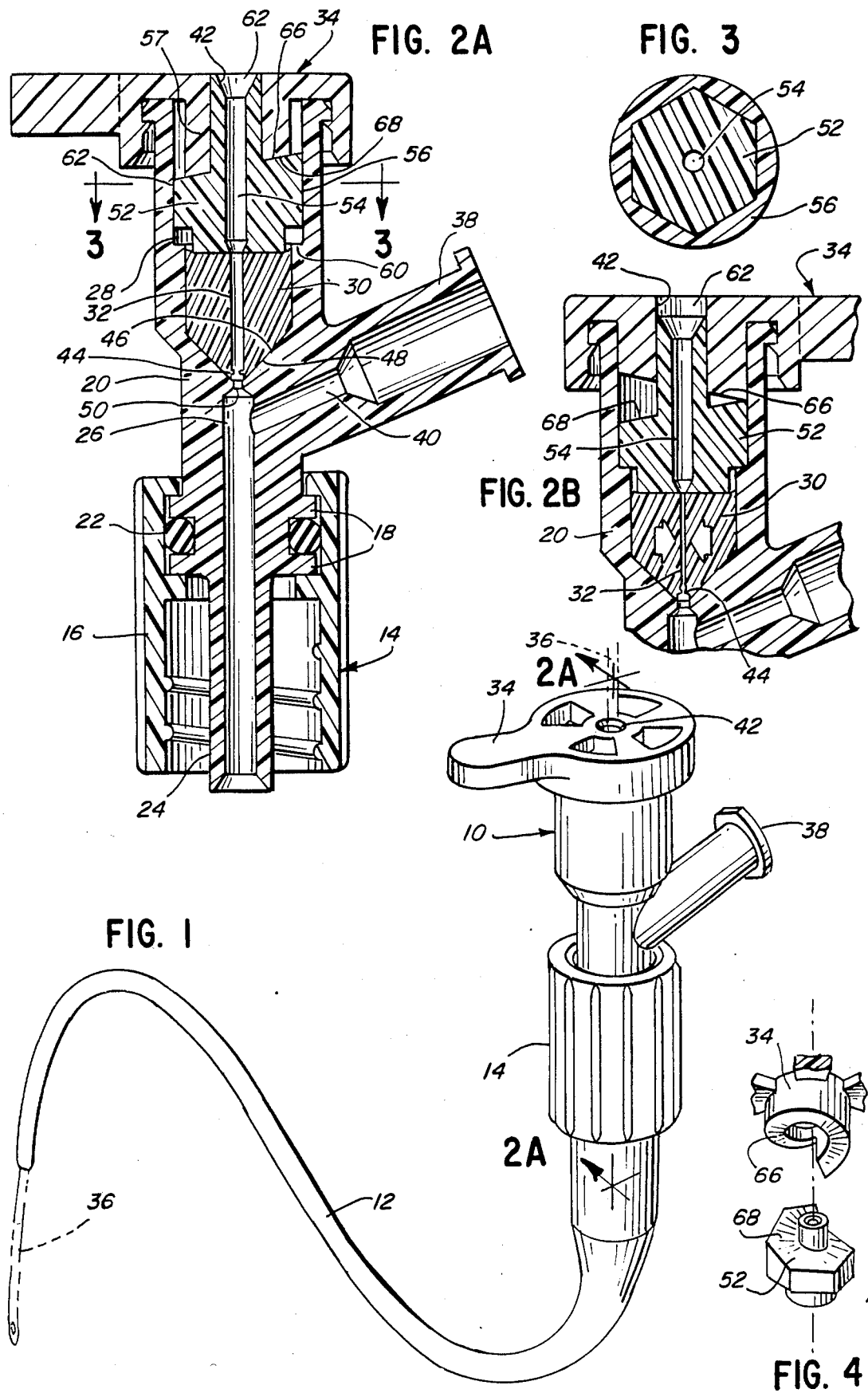

4,723,550

LEAKPROOF HEMOSTASIS VALVE WITH SINGLE VALVE MEMBER

BACKGROUND OF THE INVENTION

In Bales, et al. U.S. patent application Ser. No. 806,526, filed Dec. 9, 1985, now abandoned a hemostasis valve which is improved over other prior art versions is disclosed. Hemostasis valves are currently on catheters for performing percutaneous transluminal coronary angioplasty (PTCA), as well as angiographic procedures, for example, where x-ray contrast fluid is inserted into the coronary artery.

In PTCA, stenotic regions of coronary blood vessels are dilated by advancing a dilatation catheter through blood vessels into the stenotic region. The dilatation catheter advances over a guide wire, which guide wire moves forward, followed by the catheter, followed by another advance of the guide wire, etc. The guide wire-dilatation catheter system may be introduced through a guiding catheter to facilitate its placement.

To prevent the leakage of blood out of the proximal end of the catheter, a hemostasis valve is provided at the proximal end, to prevent seepage of blood between the guide wire and the catheter. Besides the design shown in the above-cited patent application, numerous other types of hemostasis valves are known. See for example Stevens, U.S. Pat. No. 4,000,739. Another design of hemostasis valve is the Tuohy-Borst type, making use of an adjustable, compressive sleeve which is axially compressed about the guide wire that it seals by means of a two-piece, screw threaded housing. Other designs may use an "O" ring and a tapered seat instead of a sleeve.

Many designs require tightening of the valve when high pressure X-ray contrast fluid or the like is run through the catheter. However, with such high pressure sealing, the guide wire cannot be advanced in effective manner, so the valve, such as a Tuohy-borst valve, must be loosened so that the operator can "feel" any resistance encountered by the forward advancement of the guide wire, during the operation of advancing the guide wire through blood vessels.

The degree of loosening of the valve can be critical. If excessively loosened, low pressure leakage may occur. If loosened too little, the guide wire cannot be effectively advance. Accordingly, it turns out that for the most effective performance of PTCA and angiography procedures, a hemostasis valve which is highly controllable is needed, so that the guide wire can be easily advanced, while low pressure leakage is prevented on an easy, reliable basis, without the need for great skill and experience in operation of the valve.

Thus a hemostasis valve should be provided with reliable sealing against low pressure leakage around a guide wire or the like. At the same time, an adjustable seal should also be provided which may be adjusted to seal against high pressures. Accordingly, the adjustable seal may be applied or released as desired, but, preferably, at least a low pressure seal may be constantly present to stop leakage upon release of the high pressure seal. Thus, manipulation of the high pressure seal is less critical, and requires less skill in order to avoid leakage.

Also, the surgeon who is manipulating a typical catheter for entering coronary blood vessels, for example, is overburdened with respect to things to hold and manipulate during this process. The hemostasis valve described above provides improved efficiency of adjustment of the adjustable valve, to relieve the burden on the surgeon.

While the invention of the cited patent application Ser. No. 806,526 provides improved efficiency of adjustment, it does so by the addition of a second sealing site, spaced from a first adjustable, compressible sleeve valve which is provided to give the variable pressure sealing. It is of course a complexity of manufacture to provide a second sealing site, requiring a second sleeve or gasket.

By this invention, improved efficiency of adjustment of the hemostasis valve of this invention can be provided through the use of a single, compressible tubular sleeve or gasket. In this gasket, high pressure sealing may be applied, or released, to alternatively permit the application of high pressure x-ray contrast fluid or the like, and also to permit advancement of catheters and guide wires without blood leakage through the application of a low pressure seal which remains, even when the high pressure seal is released. Despite this, the advantage remains that only a single resilient, tubular gasket is present to provide both of these functions.

Additionally by this invention, an improved structure for application and release of the adjustable, high pressurizable seal is provided.

DESCRIPTION OF THE INVENTION

In this present invention, a hemostasis valve is provided which defines a housing. The housing in turn defines a first bore extending through said housing, the housing bore defining an enlarged chamber portion which has an open outer end and which carries and retains a tubular, resilient gasket having a second bore in generally coaxial relation with the first bore.

Rotatable handle means are provided for rotating in one direction to pressurize said gasket to cause constriction of said second bore and for rotating in the opposite direction to release said pressure on the gasket to permit expansion of said second bore, whereby an elongated member passing through said bore may be subjected to a variable pressure seal.

In accordance with the invention, the bore of the tubular, resilient gasket defines at least one resilient, annular rib, whereby the elongated member passing through the tubular gasket bore may be subject at all times to at least a relatively low pressure seal from said resilient, annular rib irrespective of the pressure applied by the variable pressure seal.

The tubular, resilient gasket may define a generally conical inner end. The corresponding inner end of the enlarged chamber portion may also be of a similar, generally conical shape. The bores of the gasket and housing extend respectively through the apexes of the conical shapes of their inner ends, to facilitate registration of the bores as the gasket is compressed, specifically axially compressed.

Typically, the resilient, annular rib is located adjacent the generally conical inner end of the gasket. However, the rib may be located at other positions along the bore of said tubular gasket. Additionally, a plurality of resilient annular ribs may be provided within the bore of the gasket if desired.

The housing typically defines a branch tube for fluid flow therethrough, the branch tube being spaced from one tubular housing end by the tubular gasket.

Additionally or alternatively, the hemostasis valve of this invention may carry a particularly advantageous system for comrpessing a tubular, resilient gasket for providing a variable pressure seal against an elongated member such as a catheter end/or stylet positioned within the housing.

The housing defines a first bore extending therethrough, with the housing bore defining an enlarged chamber portion of the bore which has an open outer end, and which carries and retains the tubular, resilient gasket having a second bore positioned in generally coaxial relation with the first bore. This tubular, resilient gasket may be of the type previously described, or may be a gasket of the type used in the prior art, if desired.

A pressure member is also carried in the enlarged chamber portion at an outward position from said gasket. The pressure member defines a third bore positioned in generally coaxial relation with the first and second bores. Means are provided for permitting longitudinal motion but preventing rotational motion by the pressure member.

A rotatable cap is provided, closing the open, outer end of the enlarged chamber portion, the cap defining an aperture for access to the bores. Facing, mating spiral track means are carried on the inner face of the rotatable cap and the outer face of the pressure member, to cause pressurizing advancement of the pressure member against the tubular gasket by rotation of the cap in one direction, and release of such pressurizing advancement by rotation of the cap in the other direction.

Thus, by this means, an improvement is provided in the way by which the tubular, resilient gasket may by axially compressed, to provide the desired valving to any elongated member such as a catheter and stylet passing through the gasket bore.

Preferably, the means permitting longitudinal motion of the pressure member but preventing rotational motion are provided by causing the pressure member to define a polygonal periphery, which periphery engages a corresponding, mating, polygonal section of the chamber portion, to permit such longitudinal motion of the pressure member imparted by the rotatable cap, while preventing rotational motion.

By these means, an improved hemostasis valve may be provided, in which a single, tubular gasket provides both variable pressure sealing to an elongated member passing through its bore, so that high pressure sealing is available at any time. At the same time, the same gasket may provide a continuous, nonadjustable, second type of sealing which provides continuous, low pressure sealing (at least) irrespective of the adjustment of the variable pressure seal. Thus the disadvantages of the prior art may be overcome with the use of a single gasket member, and also an optional, novel advancing means to control the pressure on the gasket.

DESCRIPTION OF THE DRAWINGS

In the drawings,

FIG. 1 is a perspective view of one embodiment of a hemostasis valve in accordance with this invention, carried on the end of a catheter.

FIG. 2A is a sectional view taken along line 2—2 of FIG. 1, shown in condition when the tubular, resilient gasket is under reduced compressive pressure.

FIG. 2B is a fragmentary, sectional view similar to that shown in FIG. 2A, but showing the condition when the tubular, resilient gasket is compressed.

FIG. 3 is a sectional view taken along line 3—3 of FIG. 2A.

FIG. 4 is a fragmentary, exploded, perspective view of certain interior parts of the device of FIGS. 1-3.

DESCRIPTION OF SPECIFIC EMBODIMENT

Referring to the drawings, hemostasis valve 10 is shown to be attached to the end of a catheter 12 by means of a luer lock connector 14 of conventional design which connects to a corresponding, conventional luer lock connector carried on the end of the catheter.

Luer lock connecter 14 carries a rotatable threaded nut 16 which is carried by flanges 18 on the body of housing 20 of the hemostasis valve. O-ring 22 may be provided for sealing purposes, while projecting tubular portion 24 of housing 20 communicates with bore of catheter 12.

Housing 20 defines a first bore 26 of variable diameter extending therethrough. Housing bore 26 defines an enlarged chamber portion 28 which has an open, outer end as shown and which retains a tubular, resilient gasket 30 having a second bore 32 positioned in generaly coaxial relation with first bore 26.

Rotatable handle means 34 are provided for rotating in one direction to longitudinally pressurize gasket 30, to cause constriction of second bore 32. Thus, angioplasty catheter 36, or any other elongated member extending through the bore defined through hemostasis valve 10 may be radially compressed within bore 32 of gasket 30 as shown, for example, in FIG. 2B. Catheter 36 is deleted from FIGS. 2-3 for purposes of clear disclosure.

Handle 34 may be rotated in the opposite direction to release pressure on gasket 30, to permit expansion of second bore 32 as shown in FIG. 2A. Thus, any catheter or other elongated member residing in the bore 32 which passes through hemostasis valve 10 may be subjected to a radially compressive seal of variable pressure.

Tubular side arm 38 of valve 10 defines a bore 40 which communicates in branching relationship with bore 26 of housing 20. Thus, fluids such as x-ray contrast fluid may be applied through side arm 38 to the bore of catheter 12 in a PTCA procedure or the like, while valve 10 is in the configuration shown in FIG. 2B, so that highly compressed gasket 30 prevents leakage of contrast fluid around catheter 36 outwardly through the distal end 42 of hemostasis valve 10. However, when and if it is deemed advisable to advance catheter 36, which may contain a flexible stylet or the like, the pressure on gasket 30 may be released as shown in FIG. 2A to permit such advancement of the catheter through bores 32 and 26.

In accordance with this invention, to prevent backflow of blood or the like while advancing a member such as catheter 36, gasket 30 defines at least one resilient, annular, resilient rib 44 projecting into the bore 32 of gasket 30. As the result of this, when an elongated member such as catheter 36 extends through tubular gasket bore 32, and typically through the entire length of valve 10, the elongated member may be subjected at all times to at least a relatively low pressure seal from resilient, annular rib 44, irrespective of any added pressure applied by the variable pressure seal which is controlled by the position of handle 34. Thus, the leakage of blood or the like rearwardly out of proximal end 42 may be prevented, so that the surgeon does not need to worry about it as he proceeds with his PTCA surgical procedure or any other desired procedure.

If desired, added sealing rings corresponding to annular rib 44 may be placed within bore 32 of gasket 30.

Gasket 30 may define a generally conical inner end 46. The corresponding inner end 48 of enlarged chamber 28, in which gasket 30 resides, may also be of similar, generally conical shape. This facilitates the registration of the constricted portion 50 of housing 20 with bore 32 as gasket 30 is axially compressed.

Turning to the system by which gasket 20 may be compressed or released from compression as desired, pressure member 52 is also carried in enlarged chamber portion 28 at an outward or proximal position from gasket 30. Pressure member 52 defines a third bore 54 positioned in generally coaxial relation with first and second bores 26, 32. Furthermore, pressure member 52 resides in housing 20 in a manner permitting its longitudinal motion but preventing its rotational motion. This is accomplished as shown in FIG. 3 by providing polygonal configuration to the periphery of pressure member 52, and a corresponding polygonal configuration to that section 56 of the bore of housing 20 in which pressure member 52 resides. Section 56 may terminate at its distal or inner end at annular step 60, and may extend to the outer end of housing 20. Projecting inner portion 57 of handle member 34, on which spiral track 66 is found, is of small enough diameter so as not to be restricted from rotation by the polygonal bore.

Thus, pressure member 52 can be advanced and retracted to longitudinally compress gasket 30, but it cannot rotate.

Handle member 34 defines a rotatable cap, closing the open outer end of the enlarged chamber portion 28 of housing 20. Cap 34 defines an aperture 62 for access to bores 54, 32, and 26. Cap 34 may be conventionally attached by snap fit means as shown in FIGS. 2A and 2B Facing, mating spiral track means 66, 68 are respectively carried on the inner face of rotatable cap 34 and the outer face of pressure member 52, so that spiral track means 66, 68 abut each other. As handle member 34 is rotated, since handle member 34 is affixed by a snap-fit connection so that it cannot move axially, pressure member 52 is forced to move axially either in an advancing direction, to pressurize gasket 30, or a retracting direction to release such pressure. Thus control of the valving pressure of gasket 30 is achieved. Also, the presence of at least one annular sealing rib provides a certain level of continuous, low pressure sealing for a catheter 36 which extends through bore 32 in any rotational position of handle 34.

Thus, by this invention, a single, tubular gasket provides both variable pressure sealing with simultaneous, continuous, low pressure sealing, irrespective of the adjustment of the variable pressure seal. This is accomplished by a novel means for imposition and release of such variable pressure seal.

The above has been offered for illustrative purposes only, and is not intended to limit the scope of the invention of this application, which is as defined in the claims below.

That which is claimed is:

1. A guide-wire dilatation catheter system, which comprises:
   a dilatation catheter for receiving a guide-wire;
   a guide-wire;
   a hemostasis valve connected to the proximal end of said catheter; said hemostasis valve comprising a housing having a first bore extending through said housing, the first bore defining an enlarged chamber portion which has an open, outer end and which carries and retains a single, unitary tubular, resilient gasket having a second bore defined by a wall in generally coaxial relation with said first bore, the wall defining said second bore being adapted for variable compression about the guide-wire substantially throughout the entire length of the second bore; rotatable handle means for rotating in one direction to pressurize the gasket to cause constriction of the second bore and for rotating in the opposite direction to release said pressure on the gasket to permit expansion of said second bore, whereby a guide-wire passing through said bore may be subjected to a variable pressure seal, the second bore having a substantially uniform diameter throught its length except that it has at least one resilient, annular rib extending radially inwardly, whereby said guide-wire passing through said tubular gasket bore may be subjected at all times to at least a relatively low pressure seal from said resilient, annular rib, irrespective of the pressure applied by said variable pressure seal.

2. The System of claim 1 in which said tubular, resilient gasket defines a generally conical inner end, the inner end of said enlarged chamber portion being of correspondingly generally conical shape, the bores of said gasket and housing extending respectively through the apexes of the conical shapes of their inner ends, to facilitate registration of said bores as the gasket is compressed.

3. The system of claim 2 in which said resilient, annular rib is located adjacent to the generally conical end of said gasket.

4. The system of claim 2 which defines a branch tube for fluid flow in said housing, said branch tube being spaced from one tubular housing end by said gasket.

5. The system of claim 4 in which the other tubular housing end defines threaded connector means.

6. The system of claim 1 in which a pressure member is also carried in said enlarged chamber portion of the housing bore at an outward position from said gasket, said pressure member defining a third bore positioned in generally coaxial relation with said first and second bores, means permitting longitudinal motion but preventing rotational motion by said pressure member; a rotatable cap closing the open, outer end of the enlarged chamber portion, said cap defining an aperture for access to said bores; and facing, mating spiral track means carried on the inner face of said rotatable cap and outer face of said pressure member, to cause pressurizing advancement of said pressure member against the tubular gasket by rotation of the cap in one direction, and release of said pressurizing advancement by rotation of the cap in the other direction.

7. The system claim 6 in which said pressure member defines a polygonal periphery, which engages a corresponding mating, polygonal section of said chamber portion, to permit said longitudinal motion and to prevent said rotational motion.

* * * * *